United States Patent [19]
Trapp

[11] Patent Number: 5,861,027
[45] Date of Patent: Jan. 19, 1999

[54] STENT FOR THE TRANSLUMINAL IMPLANTATION IN HOLLOW ORGANS

[75] Inventor: Rainer Trapp, Graben-Neudorf, Germany

[73] Assignee: Variomed AG, Liechtenstein, Germany

[21] Appl. No.: 712,201

[22] Filed: Sep. 11, 1996

[30] Foreign Application Priority Data

Apr. 10, 1996 [DE] Germany .................. 196 14 160.5

[51] Int. Cl.⁶ .................................................. A61F 2/04
[52] U.S. Cl. .................... 623/1; 623/11; 623/12; 606/191; 606/194; 606/198
[58] Field of Search ................. 623/1, 11, 12, 623/66; 606/191–200, 157–158

[56] References Cited

U.S. PATENT DOCUMENTS

| | | |
|---|---|---|
| 3,868,956 | 3/1975 | Alfidi et al. . |
| 5,344,426 | 9/1994 | Lau et al. ..................................... 623/1 |
| 5,354,309 | 10/1994 | Schnepp-Pesch et al. ................. 623/1 |
| 5,383,892 | 1/1995 | Cardon . |
| 5,441,515 | 8/1995 | Khosravi et al. ............................ 623/1 |
| 5,449,373 | 9/1995 | Pinchasik et al. ........................... 623/1 |
| 5,496,365 | 3/1996 | Sgro .............................................. 623/1 |
| 5,569,295 | 10/1996 | Lam ............................................. 623/1 |
| 5,591,197 | 1/1997 | Orth et al. .................................... 623/1 |
| 5,632,840 | 5/1997 | Campbell ..................................... 623/1 |

FOREIGN PATENT DOCUMENTS

| | | |
|---|---|---|
| 274 846 | 7/1988 | European Pat. Off. . |
| 662307 | 7/1995 | European Pat. Off. .................. 623/1 |
| 679 372 | 11/1995 | European Pat. Off. . |
| 709 067 | 5/1996 | European Pat. Off. . |
| 709 068 | 5/1996 | European Pat. Off. . |
| 95/26695 | 10/1995 | WIPO . |

OTHER PUBLICATIONS

Van Der Giessen, et al., Endothelialization of Intravascular Stents, Coronary Stenting at the Thoraxcentre Rotterdam (1986–1994), vol. 1, No. 2, 1988, pp. 25–36.

*Primary Examiner*—Mickey Yu
*Assistant Examiner*—Francis K. Cuddihy
*Attorney, Agent, or Firm*—Pillsbury Madison & Sutro LLP

[57] ABSTRACT

A stent for the transluminal implantation in hollow organs, in particular in blood vessels, ureters, oesophagi or gall tracts, is described, having a substantially tubular body which has a plurality of apertures which are each bounded by elongated boundary elements. In each case at least two boundary elements bounding the same aperture and arranged alongside one another in the circumferential direction are extended beyond the end of the aperture and form a unitary detection element. The detection element has a greater width in the circumferential direction of the stent than each of the boundary elements.

49 Claims, 6 Drawing Sheets

STENT FOR THE TRANSLUMINAL IMPLANTATION IN HOLLOW ORGANS

FIELD OF THE INVENTION

The present invention relates to a stent for the transluminal implantation in hollow organs, in particular in blood vessels, ureters, oesophagi or gall tracts, comprising a substantially tubular body which has a plurality of apertures which are respectively bounded by elongated boundary elements.

DESCRIPTION OF PRIOR ART

Stents of this kind are used for the re-channelling of hollow organs which have been changed by disease. In doing this the stents are normally introduced in a compressed state via an insertion catheter to the position to be treated within the hollow organ, where they can be expanded by different measures to a diameter which corresponds to that of the healthy hollow organ so that a support action of the hollow organ, for example of a vessel wall, is achieved.

Depending on the manner in which the expanded state is achieved one distinguishes between balloon-expanded stents and self-expanding stents. Balloon-expanded stents are installed in a compressed state on a special balloon catheter up to the position to be treated of the respective hollow organ and are expanded there by balloon inflation (insufflation) to the desired diameter. As a result of the plastic deformation of the stent material the stent obtains its stability in the expanded state so that an adequate support action for the hollow organ is achieved.

Self-expanding stents are kept in their compressed state by the use of auxiliary means, such as, for example, membrane-like coatings, and are introduced via a catheter to the position to be treated within the hollow organ. After removal of the coating these stents expand automatically as a result of their stress to a pre-determined diameter in the hollow organ so that in this manner the support of the wall of the hollow organ is achieved. These self-expanding stents can also fundamentally be subsequently pressed against the vessel wall with the aid of a balloon catheter.

The group of the self-expanding stents also includes stents of the so-called "memory metal" Nitinol. Nitinol is a nickel-titanium alloy with temperature-dependent shape behavior. If, for example, a specific form is impressed onto a Nitinol wire and the wire is subsequently heated beyond a specific "memory temperature" then the wire obtains a "memory capability" for this shape. If one subsequently cools the so treated wire down below its conversion temperature, which is dependent on the alloy and the heat treatment, then it becomes soft and easily deformable. On renewed heating beyond the conversion temperature the wire automatically readopts the impressed shape.

Self-expanding stents of the initially named kind are, for example, produced in that slits are cut with a laser into the wall of a tubular body of small diameter, extending parallel to its longitudinal axis. These slits are displaced relative to one another in the circumferential direction so that on an expansion of the tubular body, for example by balloon inflation or by heating in the case of a stent of memory metal, diamond-like apertures arise, the longitudinal axes of which likewise extend parallel to the longitudinal axis of the tubular body.

The material of the wall of the tubular body lying between the apertures thereby forms elongated boundary elements by which the apertures are separated from one another and bounded. In order to ensure good flexibility of the stent both the width and also the thickness of the elongated boundary elements amount to about 0.2 to 0.25 mm, with it being necessary to select the width and thickness to be approximately the same size because otherwise twisting of the boundary elements would occur on expanding the tubular body which could lead to kinking of the stent.

A critical point in the use of stents lies in the fact that the stent must be positioned with millimeter accuracy within the hollow organ on being inserted because full dilation of the hollow organ can only be achieved at the location which is being changed by disease. In addition, with a diseased narrowing in the region of a side-branch of the hollow organ, the covering over of the branch channel by the stent must be avoided, so that in this case also a precise positioning of the stent must be ensured.

Furthermore, stents can start to migrate even after correct positioning within the hollow organ so that even after it has been inserted its position within the hollow organ must be capable of being checked.

Both the insertion of the stent and also the checking of the position of the inserted stent are carried out with observation on an x-ray screen on which the stent, which normally consists of metal, is visible as a bright spot. As a result of the low thickness and width of the elongated boundary elements only a relatively weak picture is, however, generated on the x-ray screen by the expanded stent, so that both the position of the partly and fully expanded stent can only be poorly recognized during the insertion or directly after the insertion and also on later checking the position of the inserted stent.

In addition the expansion of the stent normally leads to a shortening of the stent in the longitudinal direction and thus to a displacement of at least the stent ends. Since the extent of the shortening depends on the extent of the expansion and thus on the not precisely known diameter of the hollow organ the accurate positioning of the stent is made even more difficult.

A further problem of the known stent lies in the fact that on expanding of the stent by dilation of the apertures the elongated boundary elements are so strongly loaded, in particular at the connection positions between two adjacent apertures in the longitudinal direction of the stent, that fractures can arise at these points. The sharp ends which arise at these fracture positions project, in particular with a bending of the stent such as, for example, occurs during a curved implantation, beyond the wall of the stent at the outer curve radius and into the inner region of the stent at the inner curve radius. This has the consequence that injuries to the wall of the hollow organ and to the balloon of a balloon catheter that is being used can occur. These are complications which cannot be tolerated in practice.

Fracture locations of this kind can also arise with inserted stents since the stent is exposed to permanent alternating loads, for example through movements of the patients or through movements of the inner organs, which can ultimately lead to the described fracture locations. These fracture locations which can occur within the inserted stent can also not be tolerated in practice.

OBJECT OF THE INVENTION

The present invention is thus based on the object of providing a stent of the initially named kind, the position of which can be precisely determined both during the insertion and also after the insertion.

Furthermore, the object should be solved of designing a stent of the initially named kind in such a way that the occurrence by fracture locations in the stent material is prevented both during the expansion of the stent and also after the expansion of the inserted stent.

BRIEF DESCRIPTION OF THE INVENTION

The object relating to the locatability is solved in accordance with the invention, starting from a stent of the initially named kind, in that in each case at least two boundary elements which are arranged adjacent one another in the peripheral direction of the stent and bound the same aperture are made so that they extend beyond the end of the aperture and form a unitary detection element which has a greater width in the circumferential direction of the stent than each of the boundary elements.

By combining two adjacently disposed boundary elements into a unitary detection element of greater width areal material regions are provided which can be better recognised on the x-ray screen than the individual, thin, elongated boundary elements. In this way a stent in accordance with the invention can be better recognized in the expanded state on the x-ray screen and can thus be more precisely positioned than a stent of known design. Moreover, the position of an inserted stent in accordance with the invention can be precisely determined with respect to broadened detection elements.

A further advantage of a stent formed in accordance with the invention lies in the fact that through the enlarged detection elements the contact pressure acting on the inner walls of the hollow organ is reduced so that a reduced irritation or reaction of the cavity wall is achieved. This applies in particular when the detection elements form the ends of the stent, since without broadened detection elements the stent ends will, in this case, be formed by pointed ends of the boundary elements so that a large reaction of the hollow cavity wall is produced, in particular in the region of the stent ends.

In accordance with an advantageous embodiment of the invention, over essentially the entire circumferential region of the stent, at least respective pairs of adjacently disposed boundary elements each form a detection element, with the width of the detection element being in particular substantially the same as the width of two boundary elements lying adjacent one another. In this manner detection elements are generated over the entire circumference of the stent so that independently of the position of the stent in the hollow organ the detection element can be recognised in its full width from each direction of observation.

In accordance with a further advantageous embodiment of the invention alternating pairs of adjacently disposed boundary elements in the circumferential direction each form a detection element, whereas the following two boundary elements are not extended beyond the end of the aperture which they bound, with the width of the detection element in particular being substantially the same as the width of four adjacently disposed boundary elements. Since two adjacently disposed boundary elements in each case are not extended beyond the end of the aperture bounded by them, the two adjacently disposed boundary elements adjoining one another in the circumferential direction can form a four-times broadened detection element so that the stent can be better observed on the x-ray screen.

Basically speaking even more boundary elements can be extended beyond the end of the aperture bounded by them so that the detection elements can be made even broader. In the compressed state of the stent spacings can also be present between the detection elements in the circumferential direction of the stent so that the width of the detection elements can fundamentally be selected as desired, as long as they are broader than the width of an individual boundary element.

The detection elements are preferably provided at one or both ends of the stent so that on checking the stent position via the x-ray screen the ends of the stent can be recognised without problem. In this manner it is possible to reliably recognise the ends of the stent on the x-ray screen and thus to make an accurate pronouncement as to the section of the hollow organ along which the inserted stent extends. Basically it is, however, also possible to provide the detection elements at any desired position between the two ends of the stent, for example in the middle of the stent.

The object relating to the stability of the stent is satisfied in accordance with the invention, starting from a stent of the initially named kind in that the apertures are formed both in the compressed state and also in the expanded state as apertures which are extended in the longitudinal direction and in the circumferential direction of the stent; and in that connection locations of thickened design are provided between two apertures arranged adjacent to one another in the longitudinal direction of the stent.

The solution in accordance with the invention takes account of the problem that for increased stability of the stent one cannot simply arrange the slot-like apertures at greater intervals from one another so that material regions between adjacent apertures can be made broader because the width and thickness of the boundary elements present between the apertures must be of approximately the same size. If one would simply increase the spacings between the slot-like apertures then the ratio of the width to the thickness of the boundary elements present between the apertures would come out of balance so that on expanding the stent, or with alternating loading of the inserted stent, twisting of the boundary elements would occur, which could lead to kinking of the stent.

Through the solution of the invention of making the apertures not only as slots even in the compressed state but rather making them so that they are areal and by simultaneously reinforcing the connection positions formed between two apertures arranged in the longitudinal direction of the stent a situation is achieved in which the positions which are particularly loaded during expansion or during alternating loading are made more stable and simultaneously the width and thickness of the boundary elements present between the apertures can be selected to be substantially the same size. Thus a stress-optimized design is provided which unites the stability and flexibility required for a stent in an ideal manner.

In accordance with a further advantageous embodiment of the invention the connection positions which are of strengthened design are formed by broadened regions of the boundary element extending in the circumferential direction of the stent. In this manner a particularly simple and cost-favorable manufacture of a stent in accordance with the invention is made possible in that the broadened portions can be simultaneously formed, for example during generating of the cut-outs by cutting with a laser beam along a, for example, computer-controlled cut-line so that the shape of the broadened portions of the boundary elements can be simultaneously controlled by the shape of the apertures. The broadened portions of the boundary elements can, in this respect, for example be generated in such a way that the ends of the areal apertures bounded by the boundary elements taper, or in such a way that broadened regions of the boundary elements project into the apertures arranged adjacent one another in the circumferential direction.

Further advantageous embodiments are set forth in the subordinate claims.

BRIEF LISTING OF THE FIGURES

The invention will subsequently be described by way of example and with reference to the drawings in which are shown:

FIG. 1 a shortened cutting pattern illustrated flat for the generation of the apertures and the detection elements for a stent in accordance with the invention, FIG. 2 a detailed view in accordance with FIG. 1, FIG. 3 a detailed view similar to FIG. 2 of a further embodiment of a stent formed in accordance with the invention, FIG. 4 a shortened cutting pattern illustrated in a flat shape for the production of the apertures and detection elements for a further embodiment of a stent formed in accordance with the invention, FIG. 5 a detailed view in accordance with FIG. 4, FIG. 6 a detailed view in accordance with FIG. 5 of the stent in the expanded state, FIG. 7 a detailed view similar to FIG. 6 of a further embodiment of a stent formed in accordance with the invention, and FIG. 8 a schematic illustration of the side view of a stent formed in accordance with the invention.

DESCRIPTION OF PREFERRED EMBODIMENTS

Figure 1:
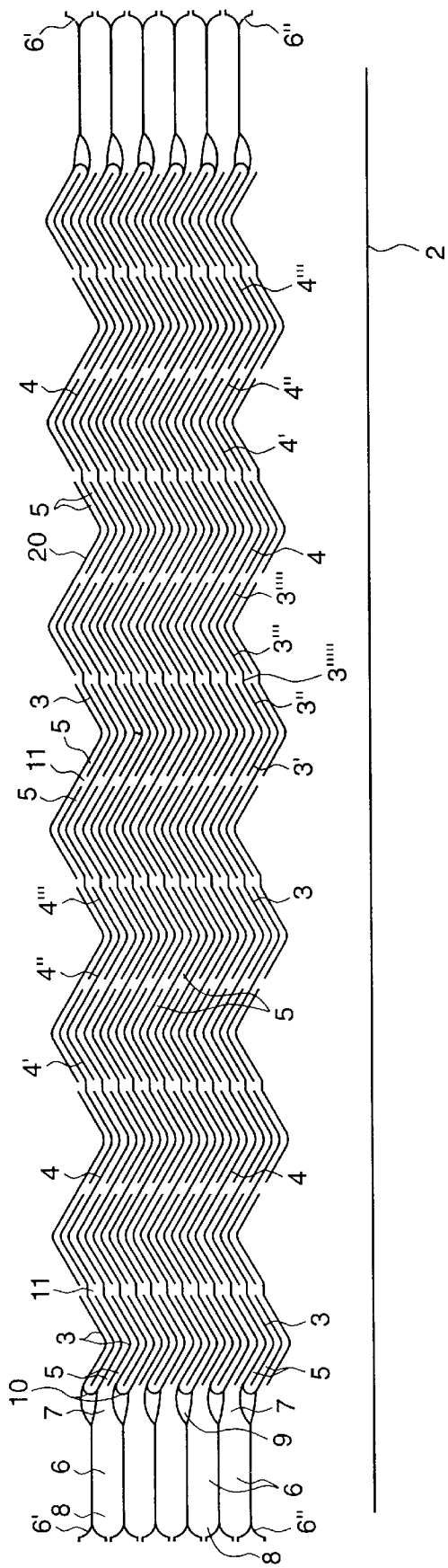
Figure 2:
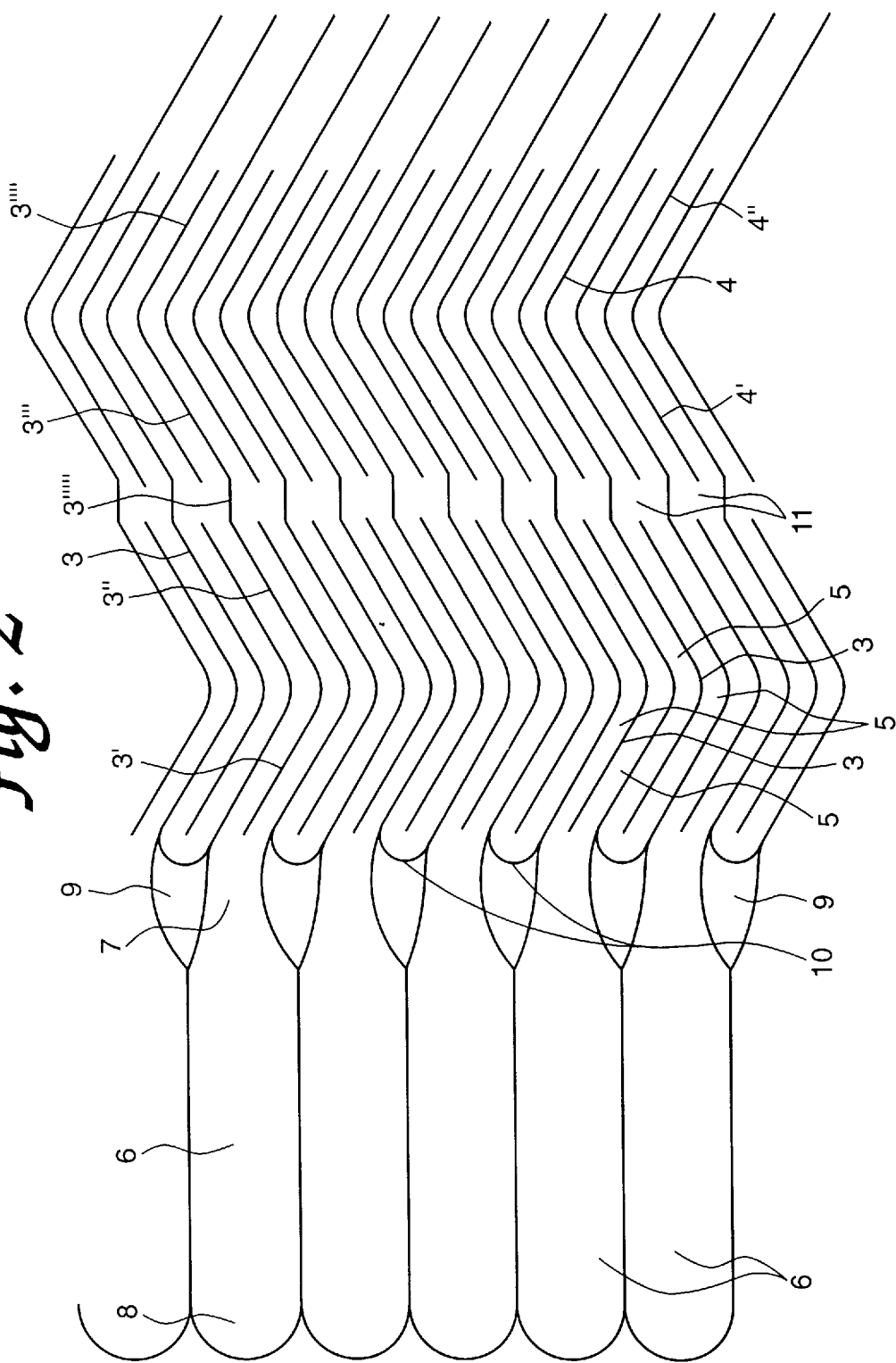

FIGS. 1 and 2 show a cutting pattern such as is cut, for example by means of a laser, into the wall of a tubular body 1 (see FIG. 8) for the manufacture of a stent designed in accordance with the invention. To make the position of the cuts clear within the wall of the tubular body 1 the course of the longitudinal axis of the tubular body 1 is provided with the reference numeral 2 in FIG. 1.

Through the cutting process apertures 3, 4 arise in the wall of the tubular body 1 which, in the compressed state, have the shape of the slit-like openings illustrated in FIG. 1.

The slit-like openings 4 have three sections 4', 4" and 4'" which are respectively arranged obliquely to the longitudinal axis 2 of the tubular body 1 and in each case form Z-like slot-like openings 4. The slot-like openings 3 have four sections 3', 3", 3'" and 3"" which are respectively arranged obliquely to the longitudinal axis 2 of the tubular body, and in each case the sections 3' and 3" and the sections 3'" and 3"" form v-shaped apertures openings which are connected together via a fifth section 3""' extending parallel to the longitudinal axis 2.

The material of the wall of the tubular body 1 lying between the apertures 3, 4 in each case forms boundary elements 5 for the apertures 3, 4. In this arrangement in each case 2 boundary elements 5 arranged adjacent to one another in the circumferential direction of the stent form a frame element 20 for an aperture 3, 4 as can be particularly clearly seen from FIG. 6.

At the two ends of the stent alternating pairs of adjacently disposed boundary elements 5 in the circumferential direction are extended beyond the end of the apertures 3 bounded by them and connected into a unitary, tongue-like detection element 6. The detection element 6 has approximately twice the width of a boundary element 5 at its end 7 connected to the boundary elements 5 and broadens in the direction towards its free end 8 to approximately four times the width of the boundary element 5, so that detection elements 6 arranged in the circumferential direction of the stent lie in contact with one another over the larger part of their length.

Between the ends 7 of two adjacent detection elements 6 there are formed cut-outs 9 into which the ends 10 of in each case two adjacently disposed boundary elements 5 open which are not extended beyond the end of the aperture 3 bounded them. The ends 10 of the boundary elements 5 can also directly contact side edges of the end 7 of the detection element 6 so that no cut-outs 9 are present.

In each case two boundary elements 5 arranged alongside one another in the peripheral direction of the stent which do not bound the same aperture 3, 4 are connected together at connection positions 11. The apertures 3, 4 generated by the cutting pattern illustrated in FIG. 1 and also the detection element 6 are uniformly distributed over the entire circumference of the tubular body 1 so that, for example, the detection elements 6' and 6" which are each half shown in FIG. 1 at the upper and lower margin form the two halves of one and the same detection element 6.

Depending on the length of the tubular body 1 more or less boundary elements 5 and apertures 3, 4 can be distributed along the longitudinal axis 2 of the tubular body 1 than are shown in FIG. 1. In corresponding manner, depending on the circumference of the tubular body 1, the number of the boundary elements 5 of the apertures 3, 4 and also of the detection element 6 can vary along the circumference of the tubular body 1.

Figure 3:
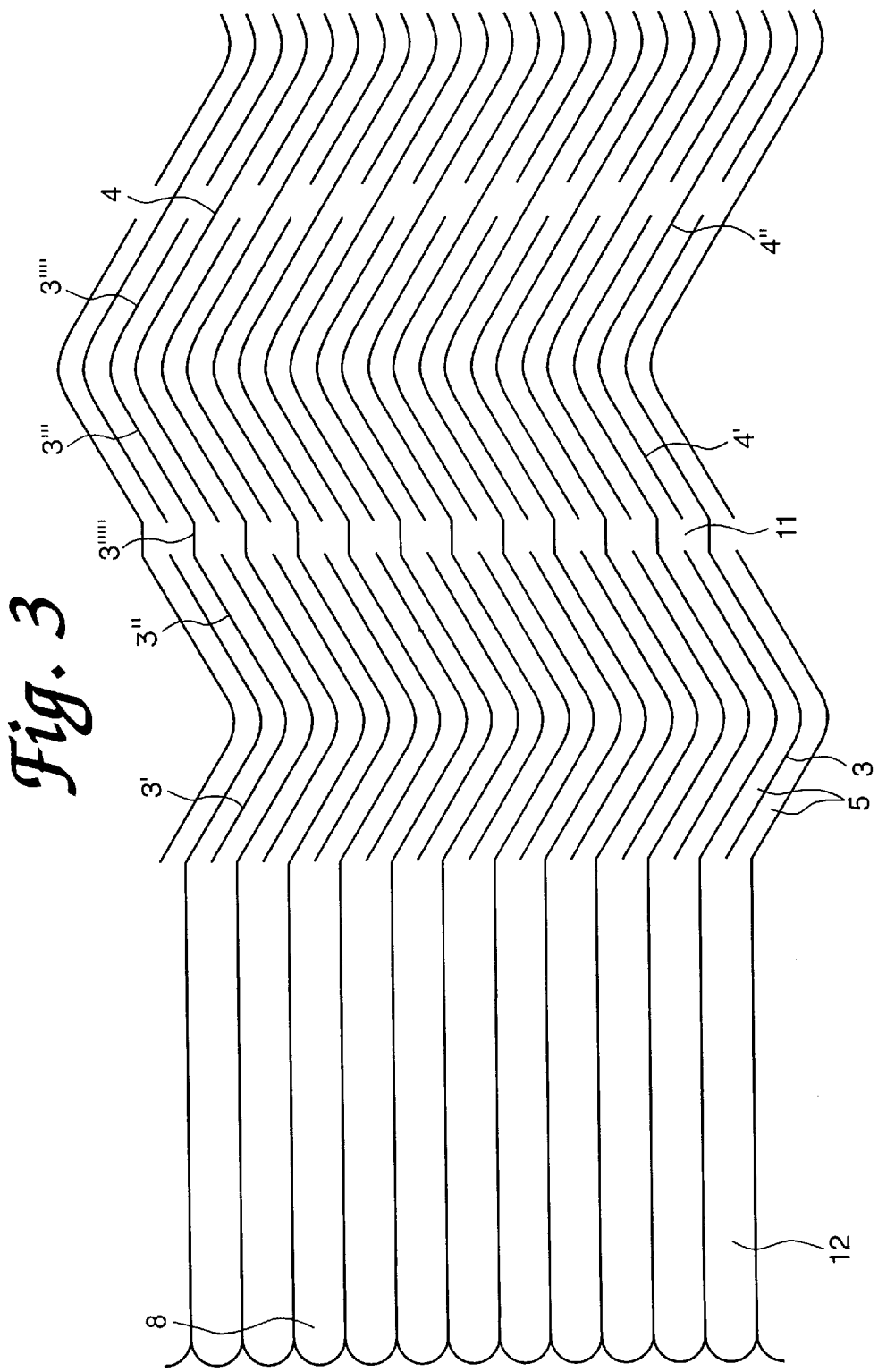

In the embodiment shown in FIG. 3 each of the boundary elements 5 disposed at the end of the stent is extended beyond the end of the aperture 3 bounded by it so that in each case two boundary elements 5 arranged in the circumferential direction form detection elements 12 which are made twice as broad as a boundary element 5. The stent of FIG. 3 thus includes more detection elements than the stent of FIGS. 1 and 2, with the detection elements 12 having a lesser width than the detection elements 6 of FIGS. 1 and 2 but having a radius of curvature which is better matched to the radius of the expanded stent.

Figure 4:
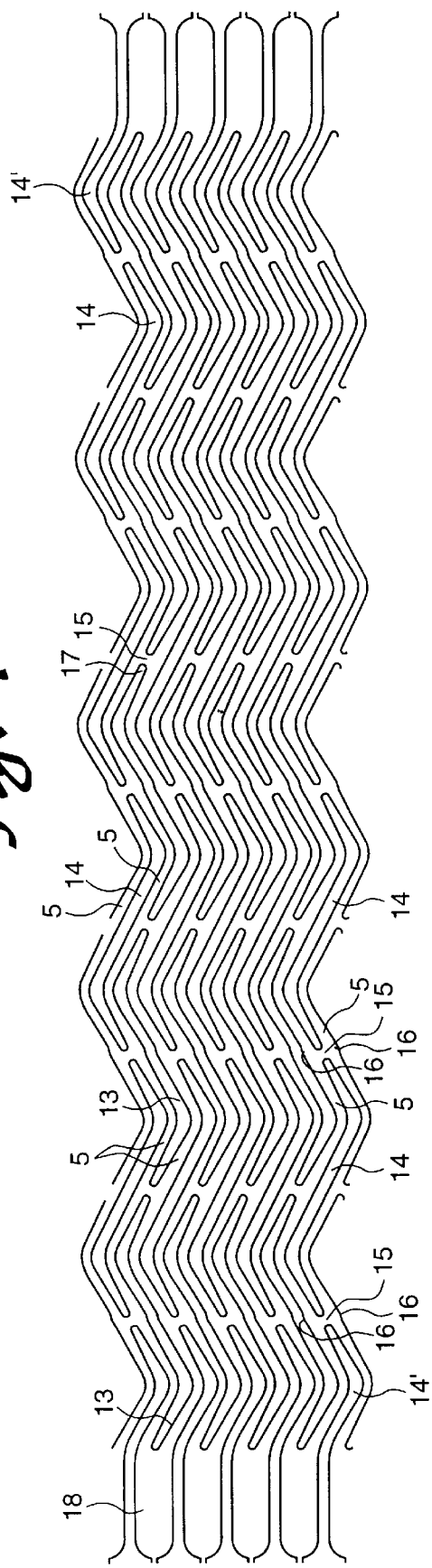
Figure 5:
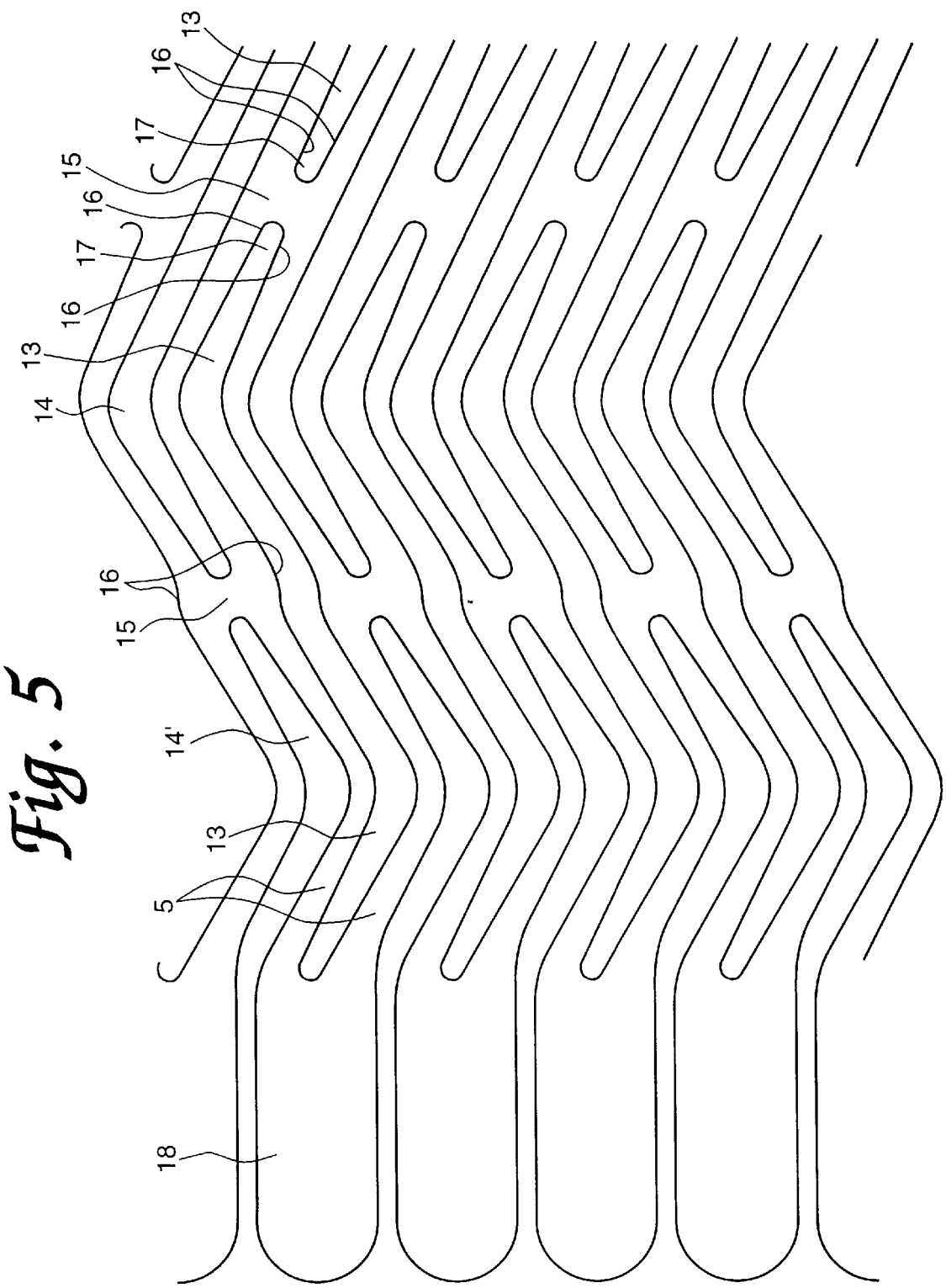

In the embodiment of FIGS. 4 and 5 the apertures are not only formed as slot-like openings but rather as areal apertures 13, 14. As in the embodiments of FIGS. 1 to 3 the apertures 13, 14 are in each case framed by two boundary elements which form frame elements for the apertures 13, 14.

Strengthened connection positions 15 are provided between in each case two apertures 14 arranged adjacent to one another in the longitudinal direction of the stent and also between the apertures 14' which are open towards the ends of the stent and the adjacent apertures 14 in the longitudinal direction, with the strengthened portions being formed as broadened portions 16 of the respective ends of the boundary elements 5 which bound the apertures 14, 14'. The contour of the broadened portion 16 can thereby extend asymmetrically between the apertures 14, 14', as is, for example, illustrated in FIG. 5. The contour can, however, also be symmetrically formed so that the mutually abutting ends of two boundary elements 5 are shaped to be substantially mirror-symmetrical.

The fact that the broadened portions 16 are provided essentially in the region between the two apertures 14 or 14 and 14' in which the largest loads can act on the boundary elements, for example during expanding of the stent, makes it possible through the thickness and width of the boundary elements 5 to be selected to have approximately the same size in the remaining extent of the boundary elements. As a result, no tilting or torsion of the boundary elements 5 arises on expansion of the stent. Through the broadened portions 16 at the connection locations between the ends of two neighboring apertures 14 or 14 and 14' it is ensured that the boundary elements 5 are made so much stronger in the region of the connection locations 15 that a breakage of the boundary elements 5 during dilation of the apertures 14 is reliably prevented.

A strengthening of the connection locations 15 can be additionally or solely achieved in that the apertures 13 are made so that they extend in a tapering manner at their ends 17, as can be seen from the FIGS. 4 and 5 so that the boundary elements are made broader in the direction towards the connection positions 15. In this manner the connection positions 15 between two adjacently disposed apertures 13 in the longitudinal direction are of strengthened shape, so that a breakage of the boundary elements 5 on dilation of the apertures 13 is prevented.

The boundary elements 5 arranged at the ends of the stent are, as in the embodiment of FIG. 3, in each case extended beyond the end of the aperture 13 bounded by them, and in each case two of the extended sections are connected to form a detection element 18, the width of which corresponds substantially to the width of the two boundary elements 5 plus the width of the aperture 13. Basically, however, alternating pairs of adjacently disposed boundary elements 5 in the circumferential direction, could, as in the embodiment of FIGS. 1 and 2, form a detection element 18, while in each case the two adjacently disposed boundary elements 5 are not extended beyond the end of the aperture 13 bounded by them.

Figure 6:
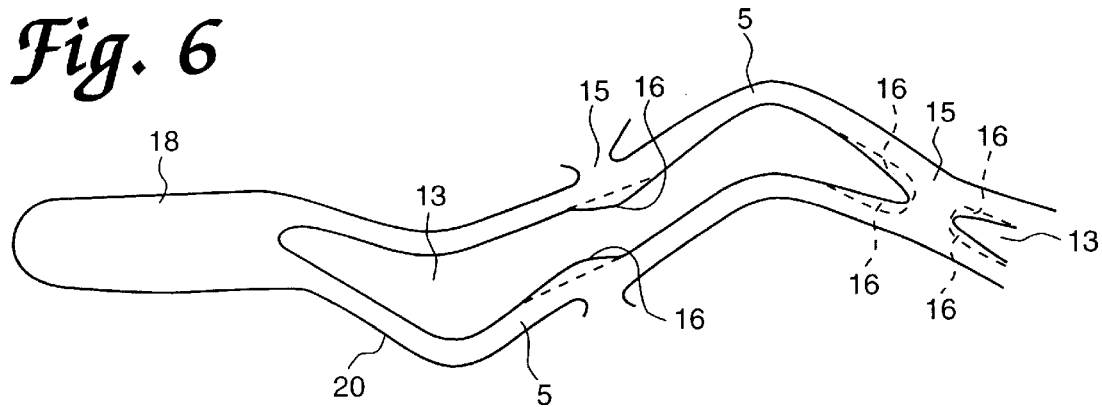

FIG. 6 shows an aperture 13 in accordance with the embodiment of FIGS. 4 and 5 in the dilated state in which an enlargement of the diameter of the tubular body 1 is achieved. Furthermore, the course of the boundary elements 5 without strengthening is drawn in in broken lines at the connection positions 15 so that the distinction over a stent without boundary elements 5 in accordance with the invention, and thus the improved loadability during bending of the boundary elements 5, can be recognized.

Figure 7:
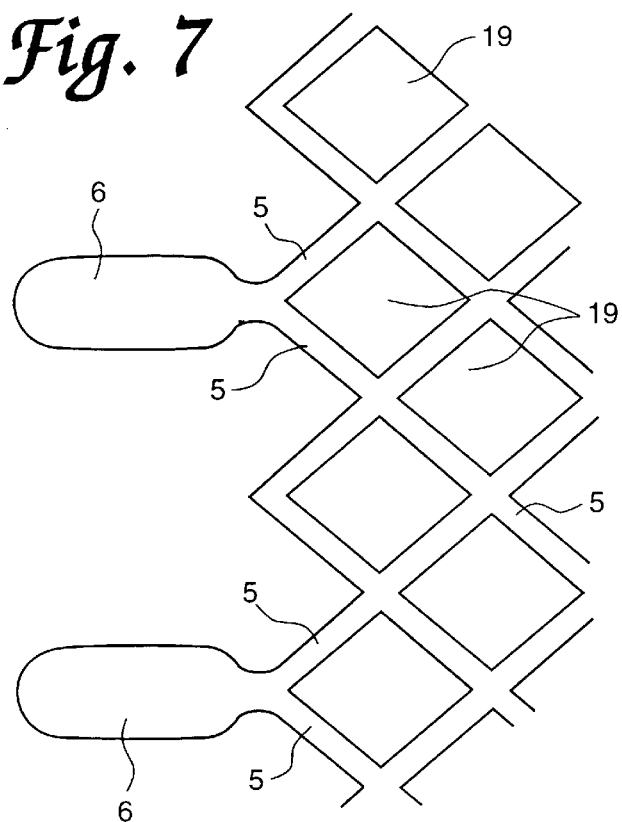

The embodiment shown in FIG. 7 of a stent formed in accordance with the invention includes diamond-like apertures 19 which arise on dilating slots cut parallel to the longitudinal axis 2 of the stent in the compressed state. In this embodiment alternating pairs of boundary elements 5 arranged in the end region of the stent are also designed so that they extend beyond the end of the apertures 19 and are combined into a leaf-like detection element 6.

Figure 8:
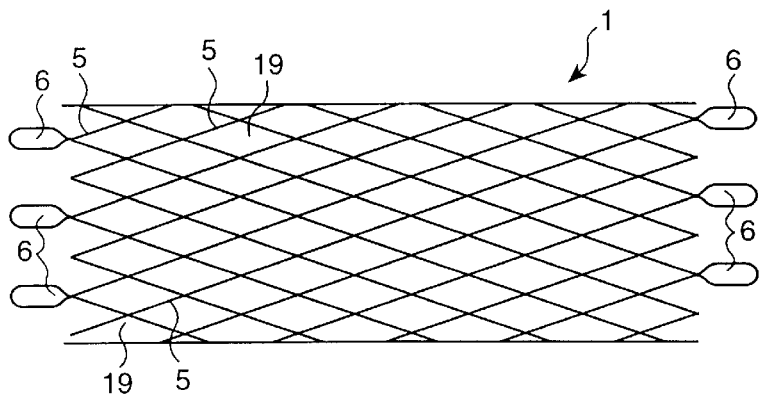

From the side view of a stent formed in accordance with the invention and illustrated in FIG. 8 the arrangement of the detection element 6 and the two ends of the tubular body 1 can be particularly well recognised.

The stent formed in accordance with the invention is preferably manufactured, prepared and used as follows:

One of the cutting patterns illustrated in the FIGS. 1, 3 or 4, i.e. slots extending parallel to the longitudinal axis 2 of the stent and displaced relative to one another, and thus the apertures 3, 4 or 13, 14 or 19, are cut into the wall of a tubular body 1 consisting of memory metal with a laser. The diameter of the tubular body 1 is thereby so selected that it corresponds to the compressed state of the stent required for implantation.

At the ends of the tubular body 1 the sheet like detector elements 6, 12, 18, which are respectively designed as extensions of two boundary elements 5 arranged adjacent to one another in the circumferential direction of the tubular body 1 and which have rounded free ends 7, are produced simultaneously with the apertures 3, 4 or 13, 14 or 19.

After the cutting pattern, or the parallel slots illustrated in FIGS. 1, 3 or 4, have been cut over the entire length and the entire circumference of the tubular body, the tubular body 1 is drawn onto an expansion mandrel, the diameter of which corresponds to the diameter of the stent required in the inserted expanded state. During this the openings 3, 4 or 13, 14, 19 respectively are broadened, as is, for example, illustrated in FIGS. 6 and 7, and on the other hand the spacings of the detector element 6, 12, 18 arranged alongside one another in the circumferential direction are enlarged relative to one another. By heating the tubular body 1 beyond the memory temperature the shape which has arisen is subsequently impressed into the material.

After cooling of the stent below the conversion temperature the stent can again be compressed to its starting diameter, corresponding to the compressed state and coated with a resilient jacket, for example of nylon, polyethylene, polyamide or of polyurethane elastomers, or can be inserted into a special catheter. The compressed stent is positioned via an insertion catheter at the desired position within the hollow organ, with the position of the stent being observed via an x-ray screen. An expansion of the stent prior to completed positioning is, for example, prevented by the elastic jacket or the special catheter. By stripping off the jacket or the catheter over a part region of the tubular body 1 the latter adopts its stored expanded state in this part region as a result of the body temperature lying above the conversion temperature. The shortening which arises as a result of the expansion thereby brings about a displacement of the exposed expanded end of the tubular body 1.

The wall region between the two ends of the stent can only be poorly recognised in the expanded state of the tubular body under the x-ray screen because this region is only formed by the pulled apart boundary elements, which are about 0.2 mm broad, and do not therefore generate any adequate image on the x-ray screen.

As the detection elements 6, 12, 18 are, however, considerably broader than the boundary elements 6, the ends of the stent can also clearly be recognized in the expanded state on the x-ray screen so that the displacement of the ends of the stent which occurs through the shortening of the stent on insertion into the hollow organ is recognized and the stent can be correctly positioned. After the stent has been fully inserted its position can once again be checked with reference to the detector elements provided at the two ends so that a wandering of the stent after correct positioning has taken place remains recognizable on the x-ray screen.

Apart from the described embodiment of memory metal the advantages of a stent formed in accordance with the invention can also be achieved when using other materials, for example tantalum, titanium, stainless steel or body-compatible plastics such as polyethylene, polyamide or polyurethane elastomers. Furthermore, the stent can also be generated through the weaving of individual, wire-like elements, for example, instead of through the generation of apertures in a tubular body.

What I claim is:

1. A stent for the transluminal implantation in hollow organs comprising:

a substantially tubular body having a plurality of apertures respectively bounded by elongate boundary elements, wherein at least two boundary elements, arranged adjacent one another in the peripheral direction of the stent, bound one aperture of said plurality of apertures and are configured to extend beyond an end of said one aperture thereby forming a unitary detection element, each unitary detection element being substantially contiguous and integral in both the longitudinal and circumferential directions of said stent, whereby the effective area of the unitary detection element material has a greater width in the circumferential direction than each of the boundary elements and also has a longitudinal length that is longer than the width of each of the boundary elements, thereby providing a way of positively locating said stent by x-ray.

2. A stent according to claim 1, wherein over essentially the entire periphery of said stent, respective pairs of adjacently arranged boundary elements each form a detection element with a width of the detection element being substantially the same as a width of two boundary elements lying alongside one another.

3. A stent according to claim 1, wherein alternating pairs of adjacently disposed boundary elements in the circumferential direction of the stent each form a detection element, wherein the width of the detection element is substantially the same as a width of four boundary elements lying alongside one another, and wherein said adjacently disposed boundary elements are not extended beyond an end of an aperture bounded by said adjacently disposed boundary elements.

4. A stent according to claim 1, wherein said unitary detection elements are provided in an end region of the stent.

5. A stent according to claim 1, wherein said unitary elements are provided in both end regions of the stent.

6. A stent according to claim 1, wherein said unitary elements form one end of stent.

7. A stent according to claim 1, wherein said unitary elements form both ends of the stent.

8. A stent according to claim 1, wherein said unitary detection element is at least substantially twice as wide in the peripheral direction of the stent as each of said boundary elements.

9. A stent according to claim 1, wherein said unitary detection element is substantially twice as wide in the circumferential direction of the stent as each of said boundary elements.

10. A stent according to claim 1, wherein said unitary detection element is substantially four times as wide in a circumferential direction of the stent as each of said boundary elements.

11. A stent according to claim 1, wherein said unitary detection elements extend substantially in the longitudinal direction of the stent.

12. A stent according to claim 1, wherein said unitary detection element is of leaf-like design.

13. A stent according to claim 1, wherein free ends of said unitary detection elements have no sharp edged sections.

14. A stent according to claim 13, wherein free ends of said unitary detection elements have a rounded shape.

15. A stent according to claim 1, wherein a length of said unitary detection elements is between about 25% and about 200% of a length of said aperture.

16. A stent according to claim 15, wherein said length of said unitary detection elements is between about 35% and about 150% of a length of said aperture.

17. A stent according to claim 16, wherein said length of said unitary detection elements is between about 50% and about 100% of a length of said aperture.

18. A stent according to claim 1, wherein said substantially tubular body can be transferred from a compressed state with a first cross-sectional diameter into an expanded state with an enlarged second cross-sectional diameter.

19. A stent according to claim 18, wherein said apertures are slot-like openings in the compressed state of the stent.

20. A stent for the transluminal implantation in hollow organs comprising:

an essentially tubular body, expandable from a compressed state having a first cross-sectional diameter into an expanded state having an enlarged second cross-sectional diameter, wherein a wall of said tubular body has a plurality of apertures enabling said expansion, wherein said plurality of apertures are configured both in the compressed state and in the expanded state as apertures which are extended in the longitudinal direction and in the circumferential direction of the stent;

wherein connection locations of thickened design are provided between two of said apertures arranged adjacent to one another in the longitudinal direction of the stent; and wherein said apertures are areal and provide a means of reinforcing the stability of the connection locations, and wherein a thickness of said wall of said tubular body is essentially equal to a width of elongated boundary elements limiting said apertures in the circumferential direction of the stent.

21. A stent according to claim 20, wherein a wall of said tubular body lying between said apertures forms frame elements for said apertures which are connected together in a longitudinal direction of the stent and which can be dilated for said expansion of the stent.

22. A stent according to claim 21, wherein said frame element comprises at least two elongate boundary elements arranged adjacent to one another in the circumferential direction of the stent and connected together at a connection location.

23. A stent according to claim 20, wherein said connection locations of thickened design are formed by broadened regions of said boundary elements extending in the circumferential direction of the stent.

24. A stent according to claim 20, wherein said apertures have a narrower width at their ends than in a region between said ends.

25. A stent according to claim 20, wherein said apertures are formed so that they extend tapering towards their ends in the compressed state of the stent.

26. A stent according to claim 23, wherein a wall thickness of said tubular body is at least substantially the same as the width of the boundary elements in their non-broadened regions.

27. A stent according to claim 20, wherein a wall thickness of said tubular body is between about 0.15 mm and about 0.30 mm.

28. A stent according to claim 27, wherein said wall thickness of said tubular body is between about 0.18 mm and about 0.27 mm.

29. A stent according to claim 28, wherein said wall thickness of said tubular body is between about 0.20 mm and about 0.24 mm.

30. A stent according to claim 23, wherein a width of the boundary elements in its non-broadened region is between about 0.15 mm and about 0.25 mm.

31. A stent according to claim 30, wherein said width of said boundary elements is between about 0.18 mm and about 0.22 mm.

32. A stent according to claim 31, wherein said width of said boundary elements is about 0.20 mm.

33. A stent according to claim 23, wherein a width of the boundary elements, in their broadened regions, is between about 0.25 mm and about 0.35 mm.

34. A stent according to claim 33, wherein said width of said boundary elements is between about 0.28 mm and 0.32 mm.

35. A stent according to claim 34, wherein said width of said boundary elements is about 0.30 mm.

36. A stent according to claim 20, wherein said unitary detection element has, in the circumferential direction of the stent, essentially the width of two boundary elements plus the width of an aperture bounded by said boundary elements.

37. A stent according to claim 1, wherein said apertures have a narrower width at their ends than in the region between said ends.

38. A stent according to claim 1, wherein said apertures are formed so that they extend tapering towards their ends in the compressed state of the stent.

39. A stent according to claim 1, wherein a wall thickness of said tubular body is at least substantially the same as a width of said boundary elements in their non-broadened regions.

40. A stent according to claim 1, wherein a wall thickness of said tubular body is between about 0.15 mm and about 0.30 mm.

41. A stent according to claim 40, wherein said wall thickness of said tubular body is between about 0.18 mm and about 0.27 mm.

42. A stent according to claim 41, wherein said wall thickness of said tubular body is between about 0.20 and about 0.24 mm.

43. A stent according to claim 1, wherein a width of said boundary elements, in its non-broadened region, is between about 0.15 and about 0.25 mm.

44. A stent according to claim 43, wherein said width of said boundary elements is between about 0.18 and about 0.22 mm.

45. A stent according to claim 44, wherein said width of said boundary element is about 0.20 mm.

46. A stent according to claim 1, wherein a width of the boundary elements, in their broadened regions, is between about 0.25 and about 0.35 mm.

47. A stent according to claim 46, wherein said width of said boundary elements is between about 0.28 and about 0.32 mm.

48. A stent according to claim 47, wherein said width of said boundary elements is about 0.30 mm.

49. A stent according to claim 1, wherein said unitary detection element has, in the circumferential direction of the stent, essentially the width of two boundary elements plus the width of an aperture bounded by said boundary elements.

\* \* \* \* \*

UNITED STATES PATENT AND TRADEMARK OFFICE
CERTIFICATE OF CORRECTION

PATENT NO. : 5,861,027
DATED : January 19, 1999
INVENTOR(S) : TRAPP

It is certified that error appears in the above-identified patent and that said Letters Patent is hereby corrected as shown below:

On the title page;

Please change

[73]     Assignee: "Variomed AG, Liechtenstein, Germany" to

--Variomed AG, Balzers, Liechtenstein--.

Signed and Sealed this

Fourteenth Day of December, 1999

Attest:

Q. TODD DICKINSON

*Attesting Officer*     *Acting Commissioner of Patents and Trademarks*